United States Patent [19]

Border

[11] Patent Number: 4,911,153
[45] Date of Patent: Mar. 27, 1990

[54] ORTHOPEDIC SURGICAL INSTRUMENT
[75] Inventor: Robert Border, Bourbon, Ind.
[73] Assignee: Biomet, Inc., Warsaw, Ind.
[21] Appl. No.: 152,292
[22] Filed: Feb. 4, 1988
[51] Int. Cl.$^4$ ............................................. A61F 5/04
[52] U.S. Cl. ........................................ 606/98; 606/64
[58] Field of Search ....... 128/92 VD, 92 YZ, 92 ZK, 128/92 YY, 92 YK, 92 YW, 92 YV, 92 YT

[56] References Cited

U.S. PATENT DOCUMENTS

| | | | |
|---|---|---|---|
| 1,201,864 | 10/1916 | Overmeyer | 128/92 ZW |
| 3,782,373 | 1/1974 | Smythe | 128/92 BD |
| 3,814,089 | 6/1974 | Deyerle | 128/92 VD |
| 3,835,849 | 9/1974 | McGuire | 128/92 VD |
| 4,103,683 | 8/1978 | Neufeld | 128/92 YK |
| 4,257,411 | 3/1981 | Cho | 128/92 VD |
| 4,341,206 | 7/1982 | Perrett et al. | 128/92 VD |
| 4,381,770 | 5/1983 | Neufeld | 128/92 YK |
| 4,418,422 | 11/1983 | Richter et al. | 378/205 |
| 4,450,835 | 5/1984 | Asnis et al. | 128/92 R |
| 4,456,004 | 6/1984 | Kenny | 128/92 R |
| 4,541,424 | 9/1985 | Grosse et al. | 128/92 VD |
| 4,622,959 | 11/1986 | Marcus | 128/92 VD |
| 4,667,664 | 5/1987 | Taylor et al. | 128/92 VD |
| 4,730,608 | 3/1988 | Schlein | 128/92 ZK |
| 4,756,307 | 7/1988 | Crowninshield | 128/92 YZ |

Primary Examiner—Robert A. Hafer
Assistant Examiner—Charles H. Sam
Attorney, Agent, or Firm—Barnes & Thornburg

[57] ABSTRACT

An orthopedic instrument serves as an adjustable guide for drills, reamers, fasteners, and other orthopedic devices which lie on a target line which extends from the lateral cortex of the femur, through an opening in the proximal end of an inserted intramedullary femoral nail, through the femoral neck, and into the femoral head. The instrument can be secured to and aligned with the inserted nail. A handle of the instrument extends downwardly from the top of the nail along a line which is substantially parallel to the target line. A guide arm is preferably slidably mounted on the handle and extends outwardly from the handle through the target line. At least one opening is formed through the guide arm coaxially with, or parallel to, the target line, for receiving a drill bit, guide tube, fastener, or similar device. When the instrument is used, for example, as a drill guide, the guide arm can be slidably adjusted along the handle to allow optimal positioning of the drill along the target line prior to the beginning of the drilling operation. Optimal positioning can be achieved regardless of patient-to-patient differences in the thickness of soft tissues covering the femur. The instrument also includes provisions for attaching a nail insertion or extraction device. This device may be attached to the instrument in line with the longitudinal axis of the nail or, alternatively, offset relative to the nail axis to provide additional clearance for the surgeon.

7 Claims, 3 Drawing Sheets 4,911,153

ORTHOPEDIC SURGICAL INSTRUMENT

BACKGROUND AND SUMMARY OF THE INVENTION

This invention relates generally to orthopedic instruments and, more particularly, to an orthopedic instrument which is especially well suited for use with an intramedullary femoral nail.

The use of nailing techniques for the treatment of fractures of the femur is well known. In cases of severe injury, fractures of the femoral neck often accompany fractures of the femoral shaft. For this reason, a number of intramedullary nails provide one or more openings in the proximal end of the nail for receiving a fastener, such as a bone screw, which extends along a line which passes through the lateral cortex of the femur, through the femoral neck, and into the subchondral region of the femoral head. An example of one such nail is shown in U.S. Pat. No. 4,622,959.

When using a nail and related fasteners of the types described in the above-referenced patent to reduce fractures of the femur and the femoral neck, it is necessary to drill one or more holes from the side of the femur through the neck and into the femoral head, along the line of the screw-receiving opening(s) formed in the proximal end of the nail. Since proper drill alignment with the opening(s) in the inserted nail can be difficult to achieve, a number of jigs and fixtures have been devised to accomplish this end. Two such instruments are shown in FIGS. 1 and 2 of this specification, and are described in detail below.

When using devices such as those illustrated in FIGS. 1 and 2 to locate and drill holes in the femur, it is desirable that the guide arm of the instrument, which normally extends downwardly and substantially parallel to the femur, be positioned as closely as possible to the soft tissues covering the femur. Instruments of the type shown in FIG. 1, in which the lateral distance between the guide arm and femur are fixed, do not allow close positioning of the guide arm to the femur, since the lateral distance between the femur and guide arm must be selected to accommodate relatively thick soft tissues typically found in obese patients. Instruments of the type shown in FIG. 2 provide for some degree of lateral adjustment, but fail to provide optimal results throughout the complete range of patient types and body sizes. Accordingly, there exists a need for an orthopedic instrument of the above-described type in which the guide arm is adjustable to accommodate the full range of patient body types. It is an object of this invention to provide such an instrument.

This and other objects are attained in an orthopedic instrument which is especially well suited for use with an intramedullary femoral nail having one or more openings in its proximal end for receiving one or more fasteners. At least one of these openings extends upwardly along a target line which passes through the lateral cortex of the femur, through the femoral neck, and into the subchondral region of the femoral head. The preferred embodiment of the orthopedic instrument of the present invention includes means for securing the instrument to the proximal end of the nail, means for circumferentially and axially aligning the instrument with the nail, a handle attached to the means for securing the instrument to the nail and extending downwardly along a line substantially parallel to the target line, and a guide arm assembly which is adjustably and movably mounted on the handle means. The guide arm assembly extends through the target line and is provided with at least one opening extending coaxially with the target line for receiving orthopedic accessories, such as drills, reaming devices, guide tubes, guide pins, or fasteners. In an especially preferred embodiment of the invention, the guide means is slidably mounted on the handle, and is provided with means for securing the guide arm assembly at selected positions along the handle.

The preferred embodiment of the present invention includes additional features, such as provision of means for attaching nail insertion or extraction devices which are used, in conjunction with the instrument of the present invention, to drive the nail into or remove the nail from the femur. Provision is made for attachment of the nail insertion or extraction tool in a position which is slightly offset, relative to the longitudinal access of the nail, to provide additional working clearance to the surgeon, if needed.

Other objects, advantages and novel features of the present invention will become apparent from the following detailed description of the invention, when considered in conjunction with the accompanying drawings.

DETAILED DESCRIPTION OF THE DRAWINGS

Figure 1:
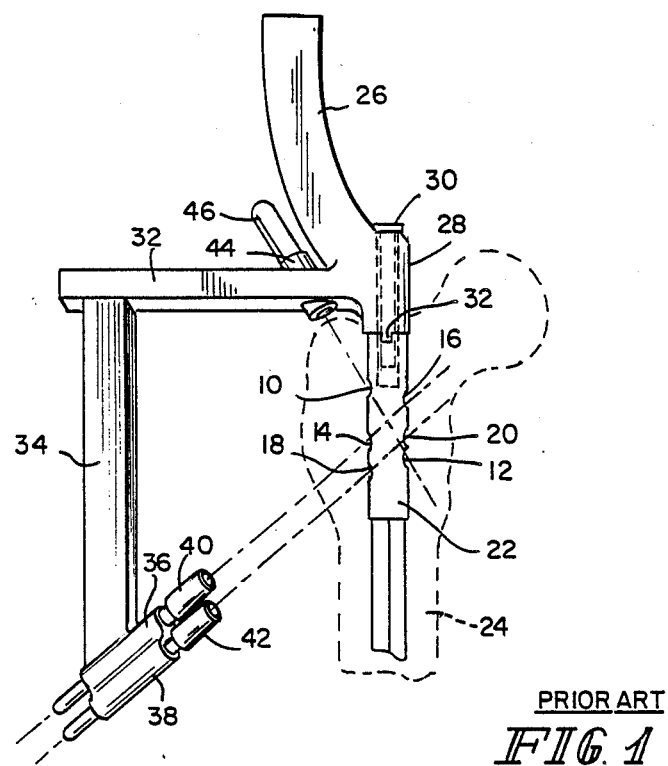
FIG. 1 is a front view in elevation of a prior art orthopedic instrument used in drilling holes and/or inserting screws in the proximal region of the femur in alignment with openings in an inserted nail.

FIG. 1 shows the screw guide and drilling jig disclosed in U.S. Pat. No. 4,622,959. The instrument of FIG. 1 is used for forming screw-receiving openings in the proximal region of the femur, in alignment with openings 10-12, 14-16, and 18-20 in the proximal end of nail 22 after nail 22 has been inserted in femur 24 of a patient. The instrument of FIG. 1 has a handle 26 and a securing head 28 which has a fastening screw 30 extending therethrough. Screw 30 has threads which mate with internal threads in the head of nail 22. Lugs 32 at the bottom of head 28 enter matching grooves in the upper end of the nail to align the instrument with nail 22 when screw 30 is fully tightened.

Extending laterally from head 28 is a bar 32, and secured to bar 32 and projecting downwardly is a guide arm 34. Fixed to the lower end of guide arm 34 are guide sleeves 36 and 38, the central axes of which are in precise diagonal alignment with the centers of openings 14-16 and 18-20, respectively. Removable bushings 40 and 42 are slidably mounted with guide sleeves 36 and 38. These bushings can be extended into the thigh of the patient to prevent damage to soft tissue during drilling or insertion of screws in the femur. Another guide sleeve 44 and bushing 46 are positioned on bar 32 in alignment with opening 10-12.

Figure 2:
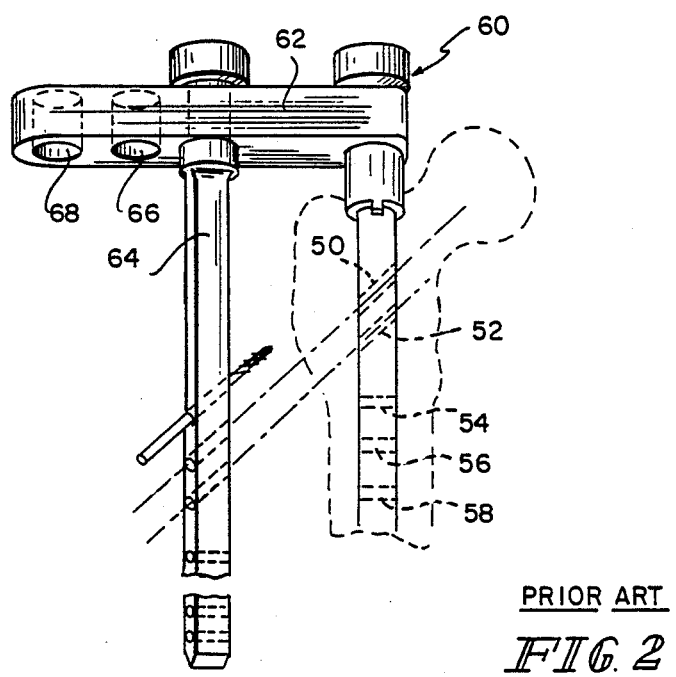
FIG. 2 is a front view in elevation of another prior art instrument used for purposes similar to those of the instrument of FIG. 1.

FIG. 2 shows another prior art device which is used in conjunction with an intramedullary nail known as the Huckstep Nail. The Huckstep Nail is formed with a plurality of angular openings 50 and 52 adjacent the femoral neck, and a plurality of transverse openings, typified by openings 54, 56 and 58, extending along substantially the entire length of the nail. The instrument or jig used in drilling holes aligned with these openings includes an attachment assembly 60 for attaching the instrument to the end of the nail, and for axially and circumferentially aligning the instrument with the openings in the nail. The instrument further includes an outwardly extending bar 62 and a downwardly extending guide arm 64. Guide arm 64 is detachably mounted in bar 62, and can be moved to positions 66 and 68 to provide for limited adjustment of the lateral distance between guide arm 64 and the femur.

Figure 3:
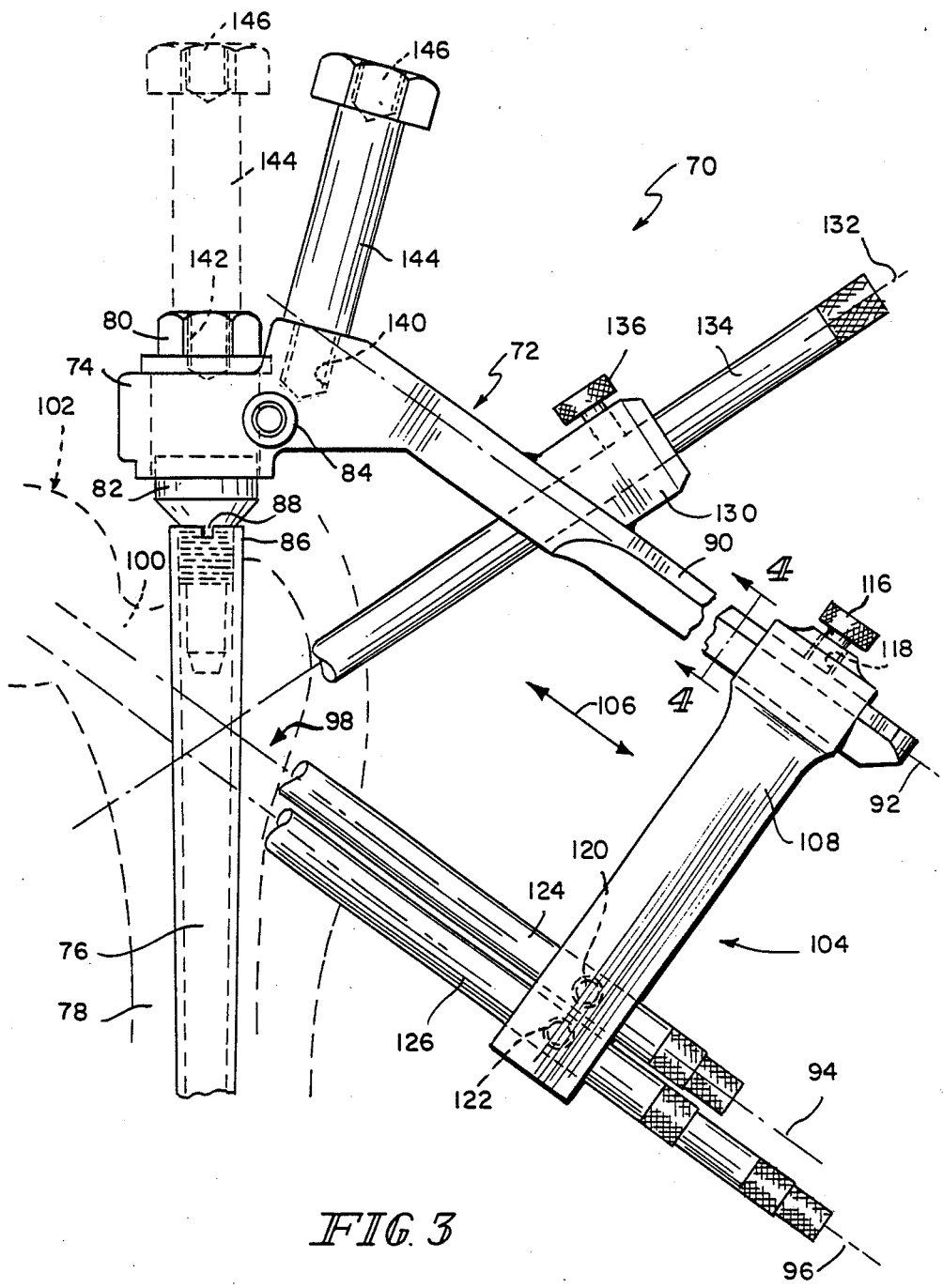
FIG. 3 shows a plain view of the instrument of the present invention.

FIG. 3 shows a front view of orthopedic instrument 70 of the present invention. Instrument 70 includes a handle 72 which has a head portion 74, which is adapted for attachment to an alignment with the proximal end of an intramedullary nail (76) which has been fitted into the medullary canal of femur 78 of a patient. In the preferred embodiment of the invention, head 74 is fitted with threaded bolt 80 which is held in head 74 by removable bushing 82. A release mechanism 84 is provided and allows for the removal of bushing 82 and bolt 80 from head 74. The details of this arrangement are not shown, and form no part of the present invention.

Bolt 80 is free to rotate in head 74 and can be threaded into internal threads located in end 86 of nail 76. Alignment lugs 88, similar to those described in connection with prior art FIGS. 1 and 2, are provided to align instrument 70, axially and circumferentially, with nail 76.

Handle 72 further includes a downwardly extending portion 90, which extends along line 92 which is substantially parallel to lines 94 and 96. Lines 94 and 96 pass through the lateral cortex of the femur, in the area generally designated by reference 98, through femoral neck 100, and into the subchondral region of femoral head 102, and represent the lines along which fasteners are typically placed to reduce fractures of the femoral neck. For purposes of convenience, lines 94 and 96 are collectively referred to below as the target line.

Figure 4:
FIG. 4 shows a sectional view of the handle of the instrument of the present invention, taken along line 4-4 of FIG. 3.
Figure 5:
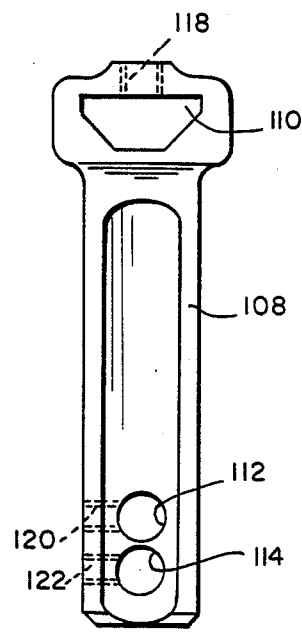
FIG. 5 shows a side view of the guide arm of the present invention.

As previously noted, portion 90 of handle 72 extends downwardly along line 92 which is substantially parallel to the target line. A guide arm assembly 104 is movably and adjustably mounted on portion 90 of handle 72. In the preferred embodiment of the present invention, guide arm assembly 104 is slidably mounted on handle portion 90 and can be adjustably positioned closer to or farther from femur 78, as indicated by arrow 106. The preferred embodiment of guide arm assembly 104 includes a member 108 (shown in detail in FIG. 5) which has a generally V-shaped opening 110 formed in one end thereof, and which has one or more circular openings 112 and 114 formed in the opposite end thereof. The shape of opening 110 corresponds to the cross-sectional shape of handle portion 90, which is illustrated in FIG. 4 by the sectional view taken along line 4-4 of FIG. 3. Thumb screw 116 is provided in threaded hole 118 of member 108 to secure guide arm assembly 104 at various points along handle portion 90. Threaded holes 120 and 122 may also be provided to aid in retaining guide tubes 124 and 126 in holes 112 and 114. Guide tubes 124 and 126 are preferably formed with a serrated edge, as shown, for securing the ends of the guide tubes to the lateral cortex of the femur.

As previously noted, the thickness of the skin and other soft tissues overlaying the lateral cortex of the femur may differ significantly from patient to patient. The arrangement just described allows guide arm assembly 104 to be adjusted as close as possible to femur 78 prior to drilling, inserting fasteners, or performing other operations for which instrument 70 may be used. These adjustments can be made while maintaining accurate alignment of guide arm assembly 104 along the target line. The arrangement of the present invention can be optimally adjusted to perform a given operation, while readily accommodating the full range of expected patient body types.

Handle 72 is further provided with guide 130 which is fixedly mounted along the top surface of handle 72, and which is used when it is desired to lock the nail in the intertrochanteric region of the femur along line 132. This option is often preferred in the absence of fractures of the femoral neck. Guide tube 134 is shown positioned in guide 130. Tube 34 may be held in place by any suitable means, such as thumb screw 136.

Handle portion 72 and bolt 80 are provided with threaded holes 140 and 142 which receive a nail insertion or extraction device (such as a slide hammer) for driving nail 76 into, or removing nail 76 from, femur 78. A driver extension 144 may also be fitted into either of these threaded holes, and the primary driving device may be fitted into threaded hole 146 in the end of extension 144. Alternatively, a mallet may be used to strike the end of extension 146 to drive nail 76 into femur 78. The provision of threaded hole 140 allows the insertion or extraction device to be attached to instrument 70 at an angle which is offset, relative to the longitudinal axis of the nail, such that the insertion or extraction device extends outwardly from the femur and the patient's body. This arrangement may provide additional needed clearance for the insertion or extraction tool in appropriate situations.

From the preceding description of the preferred embodiment, it is evident that the objects of the invention are attained. Although the invention has been described and illustrated in detail, it is to be clearly understood that the same is intended to be taken by way of illustration and example only and is not to be taken by way of limitation. The spirit and scope of the invention are to be limited only by the terms of the appended claims.

I claim:

1. An orthopedic instrument for use with an intramedullary femoral nail having a proximal end and a longitudinal axis, and having at least one opening extending transversely through said proximal end for receiving a fastener, said opening extending along a target line which defines an acute angle with said longitudinal axis of the nail, comprising:

means for securing the instrument to the proximal end of the nail;

means for circumferentially and axially aligning the instrument with the nail;

handle means, attached to the means for securing the instrument to the nail and extending along a line which defines an acute angle with the longitudinal axis of the nail when the instrument is secured to the nail, and which is substantially parallel to said target line; and guide arm means, adjustably and movably mounted on the handle means, extending outwardly from the handle means through the target line, said guide arm means having at least one opening extending coaxially along said target line for receiving at least one of a guide tube, a guide pin, a bone drill, a reaming device, and a bone fastener.

2. An orthopedic instrument according the claim 1, wherein said guide arm means is slidably mounted on the handle means, and further comprising means for securing the guide arm means at a position along said handle means.

3. An orthopedic instrument according to claim 1, further comprising means for attaching a nail insertion-/extraction device to the orthopedic instrument.

4. An orthopedic instrument according to claim 3, wherein said means for attaching a nail insertion/extraction device is coaxially aligned with the proximal end of the nail when the instrument is secured to the nail.

5. An orthopedic instrument according to claim 3, wherein said means for attaching a nail insertion/extraction device is offset, relative to the longitudinal axis of the nail, such that said nail insertion/extraction device extends outwardly from the nail.

6. An orthopedic instrument according to claim 5, wherein said means for attaching a nail insertion/extraction device is a threaded hole in said handle means.

7. An orthopedic instrument according to claim 1, wherein at least a portion of said handle means has a V-shaped cross-section, and wherein said guide arm means has a V-shaped opening for slidably receiving said portion of said handle means.

* * * * *